US011890150B2

(12) United States Patent
Harrison

(10) Patent No.: US 11,890,150 B2
(45) Date of Patent: Feb. 6, 2024

(54) METHOD OF INSTALLING A FINAL DENTAL PROSTHESIS

(71) Applicant: James Harrison, Collingwood (CA)

(72) Inventor: James Harrison, Collingwood (CA)

(73) Assignee: HARRISON PROSTHETIC CRADLE INC., Collingwood (CA)

( * ) Notice: Subject to any disclaimer, the term of this patent is extended or adjusted under 35 U.S.C. 154(b) by 1120 days.

(21) Appl. No.: 16/574,877

(22) Filed: Sep. 18, 2019

(65) Prior Publication Data

US 2020/0008903 A1     Jan. 9, 2020

Related U.S. Application Data

(60) Division of application No. 15/212,885, filed on Jul. 18, 2016, now Pat. No. 10,433,930, which is a continuation of application No. 13/648,359, filed on Oct. 10, 2012, now Pat. No. 9,408,678.

(51) Int. Cl.
| | |
|---|---|
| *A61C 1/08* | (2006.01) |
| *A61C 13/265* | (2006.01) |
| *A61C 13/225* | (2006.01) |
| *A61C 8/00* | (2006.01) |
| *A61B 6/03* | (2006.01) |
| *A61B 6/14* | (2006.01) |

(52) U.S. Cl.
CPC ............ *A61C 1/084* (2013.01); *A61B 6/032* (2013.01); *A61B 6/14* (2013.01); *A61C 1/085* (2013.01); *A61C 8/005* (2013.01); *A61C 8/0009* (2013.01); *A61C 8/0089* (2013.01); *A61C 13/225* (2013.01); *A61C 13/2653* (2013.01)

(58) Field of Classification Search
CPC ....... A61C 1/084; A61C 1/085; A61C 8/0009; A61C 8/005; A61C 8/0089; A61C 13/225; A61C 13/2653; A61B 6/032; A61B 6/14
See application file for complete search history.

(56) References Cited

U.S. PATENT DOCUMENTS

| | | |
|---|---|---|
| 2,817,900 A | 12/1957 | Glasser |
| 4,583,947 A | 4/1986 | Hazar |
| 5,018,970 A | 5/1991 | Stordahl |

(Continued)

FOREIGN PATENT DOCUMENTS

EP     2238941     10/2010

*Primary Examiner* — Yogesh P Patel
(74) *Attorney, Agent, or Firm* — Sand, Sebolt & Wernow Co., LPA

(57) ABSTRACT

A cradle, assembly, system, and method for installing a prosthesis at a surgical site. The cradle temporarily engages the prosthesis and holds it in the correct orientation and position adjacent the surgical site. An aperture is defined in the cradle and a portion of the prosthesis is received therein. In one embodiment, the cradle, assembly and system are used to install a final dental prosthesis in a patient's mouth in a single visit to the dentist's office. A securement member pins the surgical template and subsequently the cradle to the jaw. A metal sub-structure on the final dental prosthesis is received in the aperture in the cradle. Cylinders attached to implants anchored in the jaw extend through holes in the sub-structure and are bonded to the prosthesis. The cradle is detached from the jaw and from the prosthesis prior to screws being re-inserted through the cylinders and into the implants.

16 Claims, 9 Drawing Sheets

(56) References Cited

U.S. PATENT DOCUMENTS

| | | |
|---|---|---|
| 5,057,017 A | 10/1991 | Sillard |
| 5,433,606 A | 7/1995 | Niznick et al. |
| 5,451,498 A | 9/1995 | Hazen |
| 5,503,557 A | 4/1996 | Sillard |
| 5,542,847 A * | 8/1996 | Margulies ............... A61C 1/084 433/176 |
| 5,567,155 A | 10/1996 | Hansen |
| 5,927,980 A * | 7/1999 | Sillard ................. A61C 8/0048 433/173 |
| 6,079,977 A | 6/2000 | Persichetti |
| 6,116,070 A | 9/2000 | Oshida et al. |
| 6,302,690 B1 | 10/2001 | Brandhorst et al. |
| 6,537,067 B1 | 3/2003 | Wennemann |
| 6,537,069 B1 | 3/2003 | Simmons, Jr. |
| 7,806,691 B2 | 10/2010 | Berger |
| 7,950,924 B2 * | 5/2011 | Brajnovic ............... A61C 1/084 433/75 |
| 8,038,440 B2 * | 10/2011 | Swaelens ............... A61C 1/084 433/76 |
| 8,186,999 B2 | 5/2012 | Andersson et al. |
| 8,234,000 B2 | 7/2012 | Andersson et al. |
| RE43,584 E | 8/2012 | Andersson et al. |
| D710,506 S | 8/2014 | Tolentino |
| 9,173,723 B2 | 11/2015 | Harrison |
| 9,554,879 B2 | 1/2017 | Harrison |
| D833,621 S | 11/2018 | Tolentino |
| 10,278,789 B2 | 5/2019 | Llop et al. |
| 2002/0102517 A1 * | 8/2002 | Poirier ................... A61C 1/084 433/213 |
| 2003/0186187 A1 * | 10/2003 | Germanier ........... A61C 8/0048 433/173 |
| 2003/0224328 A1 | 12/2003 | Sapian |
| 2004/0219478 A1 * | 11/2004 | Harter .................... A61C 1/084 433/75 |
| 2005/0037320 A1 * | 2/2005 | Poirier ................... A61C 1/084 433/76 |
| 2005/0233276 A1 | 10/2005 | Kopelman et al. |
| 2007/0202457 A1 | 8/2007 | Ho et al. |
| 2007/0298364 A1 | 12/2007 | Cinader, Jr. |
| 2009/0220913 A1 * | 9/2009 | Geis-Gerstorfer ... A61C 8/0012 433/215 |
| 2009/0239197 A1 | 9/2009 | Brajnovic |
| 2010/0055640 A1 | 3/2010 | Van Lierde et al. |
| 2010/0173259 A1 * | 7/2010 | Vogel .................... A61C 1/084 433/72 |
| 2010/0209868 A1 * | 8/2010 | De Clerck ........... A61B 17/176 433/174 |
| 2010/0239993 A1 | 9/2010 | Baughman et al. |
| 2010/0255441 A1 | 10/2010 | Taormina |
| 2011/0129799 A1 | 6/2011 | Kwan |
| 2012/0122057 A1 | 5/2012 | Adams |
| 2012/0156638 A1 | 6/2012 | Gantes |
| 2012/0164593 A1 | 6/2012 | Bavar |
| 2013/0071811 A1 | 3/2013 | Groscurth et al. |
| 2013/0189646 A1 | 7/2013 | Hochman et al. |
| 2014/0272778 A1 | 9/2014 | Llop |
| 2014/0272780 A1 | 9/2014 | Llop |
| 2015/0010881 A1 | 1/2015 | Llop |
| 2016/0008101 A1 | 1/2016 | Harrison |
| 2016/0038255 A1 | 2/2016 | Llop |
| 2020/0008903 A1 | 1/2020 | Harrison |

* cited by examiner

METHOD OF INSTALLING A FINAL DENTAL PROSTHESIS

CROSS-REFERENCE TO RELATED APPLICATIONS

This application is a Divisional of U.S. patent application Ser. No. 15/212,885, filed Jul. 18, 2016, which is a Continuation of U.S. Patent application Ser. No. 13/648,359 filed Oct. 10, 2012, now U.S. Pat. No. 9,408,678, the entire disclosures of which are incorporated herein by reference in their entirety.

BACKGROUND OF THE INVENTION

Technical Field

This invention relates generally to medical devices and their method of use. More particularly, this invention relates to prosthetic devices or prosthetic device parts. Specifically, this invention is directed to a cradle, system and method for correctly positioning and orienting a prosthetic device at a surgical site and is most specifically directed to a cradle used to position and orient a final dental prosthesis in a patient's mouth.

Background Information

It has become more common in recent years for prosthetic devices and prosthetic device parts to be used to replace missing body parts. These prosthetic devices and parts can take a variety of forms but are generally components which are used to replace damaged or missing parts of the human body and range from devices and parts used to replace soft tissue components to fabricated replacement parts. In this description, all such components will be generally referred to a prosthetic devices but it will be understood that this term should not be narrowly construed to only be limited to particular components.

Prosthetic devices frequently require that very specialized surgery be performed to install the same at a surgical site in the patient's body. One of the issues that arise in these surgeries is that the prosthesis has to be retained in a very particular orientation and position while the specialist is securing the prostheses in place.

By way of example, one of the fields in which this has been an issue is in the installation of dental prostheses, most particularly fixed prostheses. Dentists have been replacing teeth with prosthetic devices, also referred to by the general public as "false teeth", for many years. When one tooth or a few teeth are missing, it is relatively easy for a dentist or an oral surgeon to have the missing tooth or teeth fabricated and to install the same. (In the rest of this description, the term "dentist" will be used to represent any professional who installs dental prostheses.) One of the prime reasons that this is possible is that the dentist is able to use the remaining teeth as landmarks for positioning and orienting the replacement tooth or teeth. It is far more difficult when the patient is missing all of their teeth on the upper or lower jaw or on both of the upper and lower jaws. This is because there are no fixed or immovable landmarks on that jaw for the dentist to use to correctly position and place the dental prosthetic device.

One of the systems which has been developed to try and aid dental dentists to assist edentulous patients, i.e., patients who are missing entire jaws of teeth, is that invented and marketed by Nobel Biocare AB, of Sweden as the ALL-ON-4® system. This system is covered by a number of patents including but not limited to U.S. Pat. No. 7,950,924 (Brajnovic), U.S. Pat. No. 8,186,999 (Andersson et al), U.S. Pat. No. 8,234,000 (Andersson et al), and U.S. Pat. No. RE43,584 (Andersson et al), the entire specifications of which are incorporated herein by reference.

The system will be described with reference to a patient who has been wearing a non-fixed denture. The non-fixed denture is marked with radio-opaque-markers and, while the patient is wearing the denture, a CT scan (i.e., a computed tomography scan) will be taken of the patient's mouth. The scan will pick up the radio-opaque markers. The non-fixed denture is then scanned by itself in the CT scanner and all of the data from these two scans is fed into a computer. The computer includes programing which analyses the data and generates an exact image of the denture or prosthetic it needs to create to replace the patient's missing teeth. The program allows for manipulation of the image of the scanned jaw and prosthetic so that decisions can be made as to where to place the implants that are necessary for fixing the prosthetic to the patient's jawbone during surgery. The denture shows up on the scan and can be removed or inserted as needed. When the optimum position of the implants is determined, based on the anatomical landmarks of the oral cavity and jawbone visible in the scan, the denture is then inserted back into the image to ensure that optimal anatomical placement of the implants coincides with their optimum placement within the parameters of the prosthetic. This is important to ensure that the implants and any abutments extending therefrom will emerge from the jawbone through the prosthetic in a complementary position. The implant position and angulation is then manipulated on screen to ensure that any abutments will be positioned so that they are hidden behind the teeth on the palatal aspect (upper jaw) and/or lingual aspect (tongue side on the lower jaw).

Once the position of the various components is finalized on the computer, the program generates a parts list and creates the surgical template which is able to deliver this exact placement of the implants and abutments in the patient's mouth. The computer is connected to a manufacturing assembly and it controls the fabrication of a surgical template for the dental prosthetic. In particular, the computer uses the data to generate a milled pattern replica out of a clear composite resin which is identical to the denture relative to the tissue-fitting surface and border extensions. The surgical template is fabricated to the exact specifications determined by the scans. Special holes are drilled into the surgical template during fabrication to indicate the positions at which the implants must be placed to anchor the prosthetic into the patient's jaw. The ALL-ON-4 system made by Nobel Biocare requires only four implants to anchor a fixed prosthetic properly. The implants are meant to be placed into the jawbone in very precise locations and at specific angles that are determined by the computer. The computer also designs the prosthetic and once the implants are installed, the prosthetic is engaged with the implants.

Nobel designed this system with the intention that after the initial scans and production of the surgical template and prosthetic, the actual installation of the fixed prosthetic would be accomplished in a single visit to the dentist's office. But, the system does not function in this fashion in reality. The problem appears to originate in the fact that while the computer is incredibly accurate in creating the surgical template and the final prosthetic, the human dentist is less accurate than the system requires—simply because they are human. When the surgical template is positioned in the patient's mouth, it is seated on the gum tissue. When the dentist drills the hole in the jawbone for any one of the implants, the gum tissue may deform, thereby slightly shifting the location or the angle at which the implant is installed in the jaw. Additionally, implants are designed to be torqued to a very specific tolerance (i.e. they have to be rotated a very specific number of turns). If they are rotated even slightly more than they should be they can be inadvertently countersunk in the jaw. They may also be under-rotated into the jaw, rendering the implant too high. Dentists will also frequently adjust the torque on the implants once the surgical template is removed. Then when the prosthesis is engaged with the implants, it will not be seated properly. When this seating imbalance occurs, too much load is placed on one or more of the implants and they will tend to fail fairly rapidly. At the same time, the fixed prosthesis will not function properly as it will tend to move and put pressure on the patient's jaw.

Because of these problems, the Nobel system is used differently in practice. It has become necessary for the dentist to install the implants and the final fixed prosthetic device in separate visits. In the first visit, the dentist will take all of the necessary CT scans and will send the data to Nobel Biocare for fabrication of the surgical template. In the next visit, the dentist will install the implants in the jaw, attach temporary cylinders to the implants, and then place a temporary denture, also known as a transitional prosthesis, around those cylinders. In this previously known method of installation, as part of the procedure, it is necessary to use pre-fabricated temporary cylinders of uniform size to link the transitional prosthesis to the implants because of the issues with the installation of the implants. When these temporary cylinders are bonded to the transitional prosthesis, they typically have to be cut down so that they are substantially flush with the mouth-facing wall of the transitional prosthesis so as not to potentially injure the patient during use.

Transitional prostheses are typically of fairly poor quality as they are not meant to last more than a few months while ossification of the implants occurs, i.e., while bone grows around the implants. It takes a great deal of time and effort to even install the transitional prosthesis because of the previously mentioned issues with the installation and/or degree of torque of the implants. As a result, it has become commonplace for dentists to hand this job over to dental technicians. A transitional prosthetic is fabricated from acrylic and this components does not include a metal sub-structure. The material used in the transitional prosthesis allows the dental technician to seat, grind, shape, and cut the transitional prosthesis until it fits adequately around the cylinders on the patients' jaw. It can take several hours of time and considerable effort to even get these temporary devices to fit. The patient then has to go away for several months, living with these inferior prostheses while they wait for bone to grow around the implants and secure them in place. Previously known temporary or transitional prostheses are notorious for having poor aesthetics, bite issues causing chewing problems, discomfort and they are known for premature failure during use.

When the patient returns to the dentist for yet another visit, the implants have become embedded in the jaw and the dentist will take a new impression of the patient's jaw and implants. This impression is used to fabricate the final prosthetic device which will fit the actual position of the implants that were previously placed in the patient's jaw. This actual position tends to differ significantly from the original position the computer calculated because the tolerances involved are so tight. The final prosthetic device is comprised of a titanium sub-structure onto which is attached fabricated teeth and a simulated gum. The teeth and simulated gum are fabricated from acrylic or porcelain and are secured to the titanium sub-structure. The titanium sub-structure strengthens the final prosthetic device. After finalizing the design of the prosthetic device, the computer controls the production of the titanium sub-structure. A dental laboratory will typically be utilized to attach the teeth and simulated gum to the sub-structure and then the final prosthetic device is shipped back to the dentist for insertion.

The computer program will also generate a list of the required fixtures and fasteners for securing the transitional prosthesis to the implants and a second list of the required fixtures and fasteners for securing the final prosthesis to the implants. In this previously known system, the various components for the dentist are shipped in at least two shipments. The first shipment includes the surgical template and the implants from Nobel Biocare and the transitional prosthesis from the dental laboratory. The second shipment, which is shipped several months later, includes the final prosthesis and the second group of fixtures and fasteners. It should be noted that the transitional prosthesis has to be substantially altered and modified after implant placement with unpredictable results as previously described. Furthermore, the final prosthesis is only fabricated after a complete round of separate appointments including appointments for taking impressions, bite registration, and trying on of the prosthesis prior to finishing, in order to check aesthetics and bite. The final prosthesis is only then fixed in place by the dentist in a separate final appointment. The entire process from start to finish takes approximately one year to complete.

The above description applies to a guided installation procedure. It is also possible to install a fixed prosthesis using an unguided or freehand installation procedure. In previously known freehand or unguided installations a computer is not utilized to scan a patient's mouth, compile and analyze data accumulated during a scan, nor is a computer used in the fabrication of the surgical template, the transitional prosthesis, or final dental prosthesis. Previously known freehand installations include the following steps. Firstly, the dentist takes an impression of the patient's oral cavity and takes relevant X-rays. The dentist or a dental technician will then make a plaster model from that impression and will craft a surgical template, and a temporary dental prosthesis based on the plaster model. Bite registration, a try-in and X-rays help the dentist determine the best placement of implants and that information will be transferred onto the model in order to correctly position holes on the template and fabricate a transitional prosthesis. The implants are installed using the template and a transitional prosthesis is arduously adapted to temporary cylinders which are screwed to the implants. Several months later after osseointegration, impressions are taken yet again and the final dental prosthesis is fabricated and installed on the osseointegrated implants. While this freehand or unguided procedure works, it takes a substantial amount of labor and time for the patient to finally be fitted with their fixed prosthesis.

There have been many attempts over the last several years to resolve the issues identified above so that the procedure of installing the final prosthesis, as originally conceived, can be accomplished in a single visit to the dentist. None of the fixes proposed in the art have been successful.

There is therefore a need in the art for a device and system which will align the position of the final prosthetic device with the implants in a reliable fashion, thereby simplifying the installation of the final prosthetic device and thus substantially reducing the time and effort required to complete this installation.

BRIEF SUMMARY OF THE INVENTION

The present invention comprises a device and system which uses the Nobel Biocare ALL-ON-4 system but modifies it so that the system will now work in the way it was originally conceived. The device and system of the present invention cuts down the number of visits the patient has to make to the dentist and enables the dentist to install the implants and the final fixed prosthesis in a single visit. The patient can come in completely toothless and leave with their final fixed prosthesis safely and properly installed in a matter of hours.

The device, system and method of the present invention include all of the previously mentioned elements of the Nobel Biocare ALL-ON-4 system plus a new component, a cradle. The cradle engages a portion of the prosthesis and retains the same adjacent a surgical site in a desired orientation and position during installation of the prosthesis. In particular, the cradle is configured to engage a final dental prosthetic device and is then used to position and orient the same on the patient's jaw. The cradle particularly positions and orients the final prosthesis in the oral cavity in exactly the same position as was designed on the computer and in the lab. In essence, the cradle is a docking station that creates a fixed, immovable landmark by which to precisely orient the final prosthesis in the mouth. Additionally, the final prosthesis includes holes that are fabricated to be slightly bigger than the diameter of the titanium cylinders on the implants. This disparity allows the final prosthesis to slide, without interference, down over the cylinders until the prosthesis clicks into the cradle.

The invention therefore comprises a cradle, assembly, system, and method for installing a prosthesis at a surgical site. The cradle temporarily engages the prosthesis and holds it in the correct orientation and position adjacent the surgical site. An aperture is defined in the cradle and a portion of the prosthesis is received therein. In one embodiment, the cradle, assembly and system are used to install a final dental prosthesis in a patient's mouth in a single visit to the dentist's office. A securement member pins the surgical template and subsequently the cradle to the jaw. A metal sub-structure on the final dental prosthesis is received in the aperture in the cradle. Cylinders attached to implants anchored in the jaw extend through holes in the sub-structure and are bonded to the prosthesis. The cradle is detached from the jaw and from the prosthesis prior to screws being re-inserted through the cylinders and into the implants.

In a first aspect, the invention is a cradle which engages a portion of a prosthesis and retains the same adjacent a surgical site in a desired orientation and position during installation of the prosthesis.

In another aspect, the invention is an assembly for installing a prosthesis at a surgical site in a patient's body, where the assembly includes: a surgical template which is temporarily positioned over the surgical site and configured to identify one or more locations in the surgical site for engagement of one or more anchoring members therein; and a cradle positioned over the surgical site once the surgical template is removed; said cradle being temporarily engaging a portion of the prosthesis and retaining the same adjacent the surgical site in a desired orientation and position.

In yet another aspect, the invention is a system for installing a final dental prosthesis at a surgical site on a patient's jaw, said system comprising: a computer; programming installed in the computer; data gathered during a series of CT scans and being manipulable by the programing to cause one or more of a plurality of components to be fabricated; and wherein the one or more of the plurality of components includes: a surgical template; the final dental prosthesis; and a cradle which temporarily engages the final dental prosthesis and orients and positions the same adjacent the surgical site on the patient's jaw.

In a first method of performing the invention, a final prosthesis is installed at a surgical site in a patient's body following the steps of: installing one or more implants in the patient's jaw; placing a cradle on the jaw and over the implants; positioning and orienting the final prosthesis using the cradle; and fixing the final prosthesis to the one or more implants; wherein the entire process from the installation of the one or more implants to the fixing of the final prosthesis thereto occurs in a single visit to the dentist's office.

Yet another method of performing the invention includes the steps of: installing one or more anchoring members at the surgical site; placing a cradle adjacent the surgical site and over the implants; positioning and orienting the prosthesis using the cradle; and fixing the prosthesis to the one or more anchoring members.

BRIEF DESCRIPTION OF THE SEVERAL VIEWS OF THE DRAWINGS

A preferred embodiment of the invention, illustrated of the best mode in which Applicant contemplates applying the principles, is set forth in the following description and is shown in the drawings and is particularly and distinctly pointed out and set forth in the appended claims.

Similar numbers refer to similar parts throughout the drawings.

DETAILED DESCRIPTION OF THE INVENTION

As indicated previously, the inventor contemplates that the device, system and method of the present invention will be useful for installing a wide variety of prosthetic devices. By way of example, the following description relates to the installation of a fixed dental prosthesis utilizing the device, system and method of the present invention. It will be understood, however, that the installation of other prosthetic devices utilizing a cradle or docking station type device to engage the prosthetic and correctly orient, position and hold that prosthetic at a surgical site to enable anchoring devices to be correctly secured thereto are also contemplated to fall within the scope of the present invention.

Dental prosthetic devices are installed in patients' mouths using one of two possible procedures. The first procedure will be referred to as "guided installation" and the second procedure will be referred to as "freehand or non-guided installation". Guided installation is an installation utilizing the previously discussed Nobel Biocare system. Freehand installation is an installation where the prosthetic device is fabricated without the use of CT scans, computer's etc., where the dentist determines the placement of implants etc. This description will focus initially on the guided procedure and then on the freehand procedure.

Figure 1:
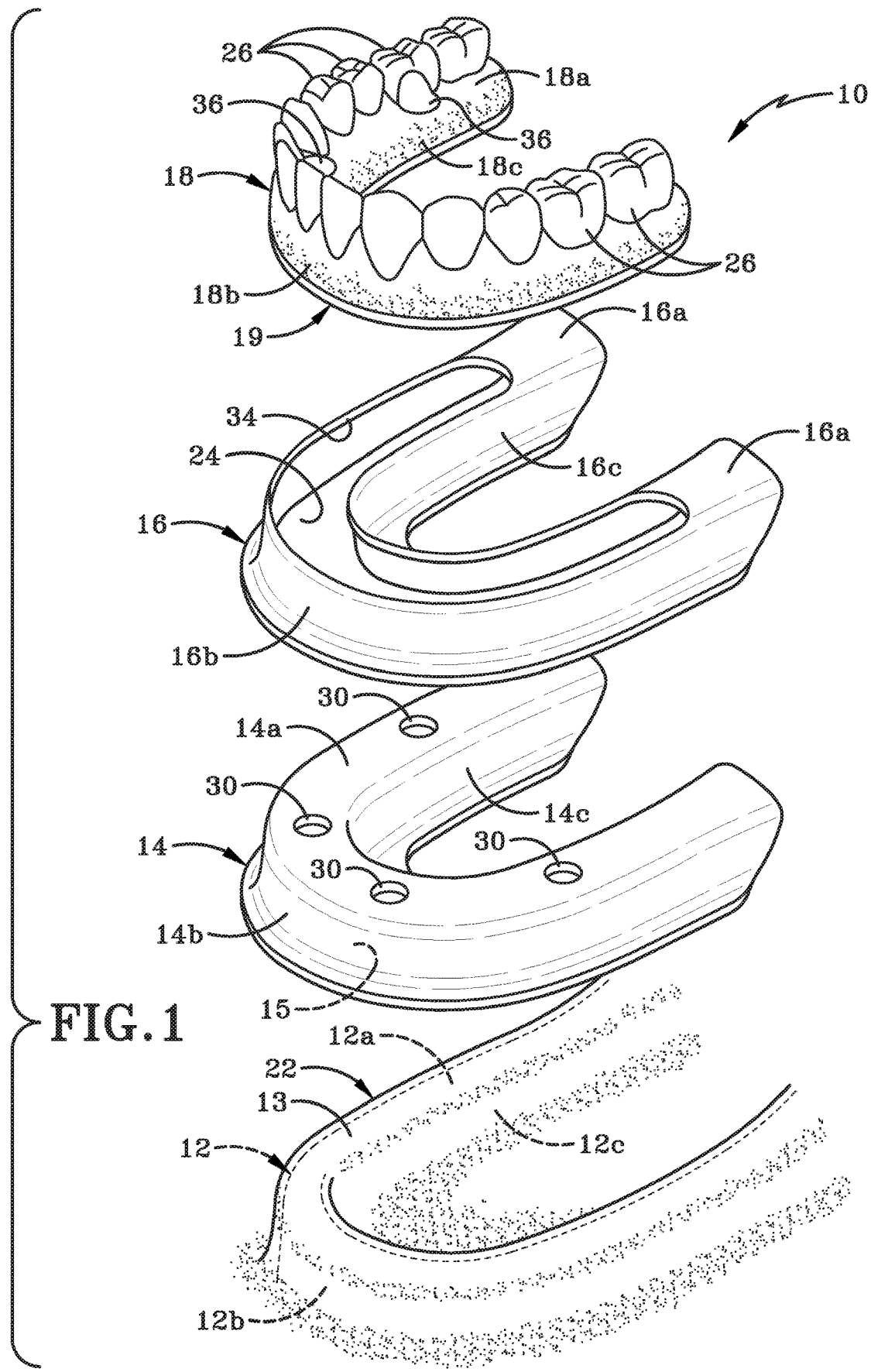
FIG. 1 is an illustrative exploded perspective view of a system in accordance with the present invention including a surgical template that is exploded away from the patient's jaw, a cradle, and the final dental prosthesis.

Referring to FIG. 1 there is shown an exploded dental prosthetic system in accordance with the present invention, generally indicated by the reference number 10. System 10 is shown by way of example only as being configured for installation on a patient's lower jawbone 12 but it will be understood that the system and components could be used on a patient's upper jawbone or partial regions of either of the upper and lower jawbones. It should also be understood that the figures are illustrative of the principles of the invention and the exact shape of the various components will be fabricated to be complementary to the patient's exact oral configuration. The figures therefore should not be construed as limiting the scope of the invention insofar as the shape of the various components is concerned.

In accordance with the present invention, system 10 comprises a surgical template 14, a cradle 16, and a dental prosthesis 18. The dental prosthesis 18 preferably is not a transitional prosthesis but is, instead, the final or fixed prosthesis to be installed in the patient's mouth as their "permanent" set of teeth. System 10 further includes at least one, and preferably four, anchoring members. The anchoring members, in the case of a dental prosthesis 18, are implants and are referenced in the figures by the number 38. (It will be understood that any suitably configured implant or other suitable fastener for securing the final prosthesis to a surgical site 13 is contemplated to fall within the scope of the present invention.) The surgical template 14, cradle 16, prosthesis 18 and anchoring members, i.e., implants 38, are configured to be used in such a manner that a patient can be taken from an edentulous state (i.e. toothless) or partially edentulous state, to having the final fixed dental prosthesis 18 fully installed in a matter of hours and in a single visit to the dentist's office.

It will be understood that surgical template 14, prosthesis 18 and anchoring members (implants 38) and their previously known methods of use in both guided and freehand installations are well known in the art and have been described in the Background section of this application. Consequently, the following description will relate to the surgical template 14, final prosthesis 18 and implants 38 only in sufficient detail to assist in understanding the present invention and how it is used. What will be further described herein are any changes to these components or the way they are used and which changes have been made in accordance with the present invention.

Cradle 16 is novel and, to the inventor's best knowledge, is not known in the art. Thus, the present invention is directed to cradle 16, a dental system for installing a final prosthesis 18 utilizing cradle 16, a kit incorporating cradle 16, and a method of installing a final prosthesis 18 which includes using cradle 16 to position and orient the prosthesis 18. Still further, the present invention is directed to a device and method for correctly orienting and positioning a prosthetic device on a surgical site on a patient's body, particularly to a device and method for placing a fixed or final dental prosthetic on a patient's upper or lower jaw.

The template, 14, prosthesis 18 and anchoring assemblies 38 which are known will now be described in somewhat greater detail and in particular with reference to their use in a guided installation. As has been described in the Background of this application, surgical template 14 and prosthesis 18 are fabricated after data relating to the patient's upper or lower jaw and any previously worn non-fixed or fixed dentures have undergone CT scanning.

Still referring to FIG. 1 surgical template 14 as illustrated is configured to be seated on the patient's lower jaw and comprises a first wall 14a, a first sidewall 14b and a second sidewall 14c. First and second sidewalls 14b, 14c extend outwardly away from first wall 14a and define a channel 15 therein which is configured to follow an exterior contour of the gum tissue 22 surrounding the patient's jawbone 12. The first wall 12a of the patient's jawbone covered by tissue 22 comprises the surgical site 13 onto which final prosthesis 18 is to be installed.

When surgical template 14 is seated on the patient's lower jaw, the interior surface of first wall 14a of template 14 will be seated on tissue 22 on top surface 12a of jawbone 12, i.e., on surgical site 13. The interior surface of first sidewall 14b will be disposed adjacent the front region 12b of jawbone 12 and second sidewall 14c will be disposed adjacent the rear region 12c of jawbone 12. Surgical template 14 is fabricated to define at least one aperture 30 therein. Preferably, template 14 defines four apertures 30 therein, with each aperture 30 being in a specific location selected by the computer program and the dentist manipulating that program. (In other applications, the final prosthesis may require more implants to anchor it and the surgical template 14 will then be provided with that complementary number of apertures 30.) The location of each aperture 30 indicates to the dentist the exact position in which he or she needs to drill pilot holes 32 (FIG. 5) for placement of one of the implants 38, as will be hereinafter described. The dimensions of surgical template 14 are exact and apertures 30 in template 14 are exactly sized to receive implants 38 therethrough.

Figure 3:
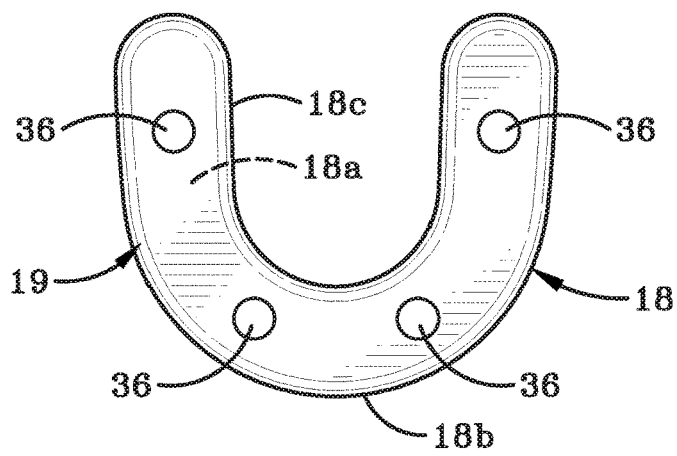
FIG. 3 is a bottom view of the final dental prosthesis shown in FIG. 1.
Figure 4:
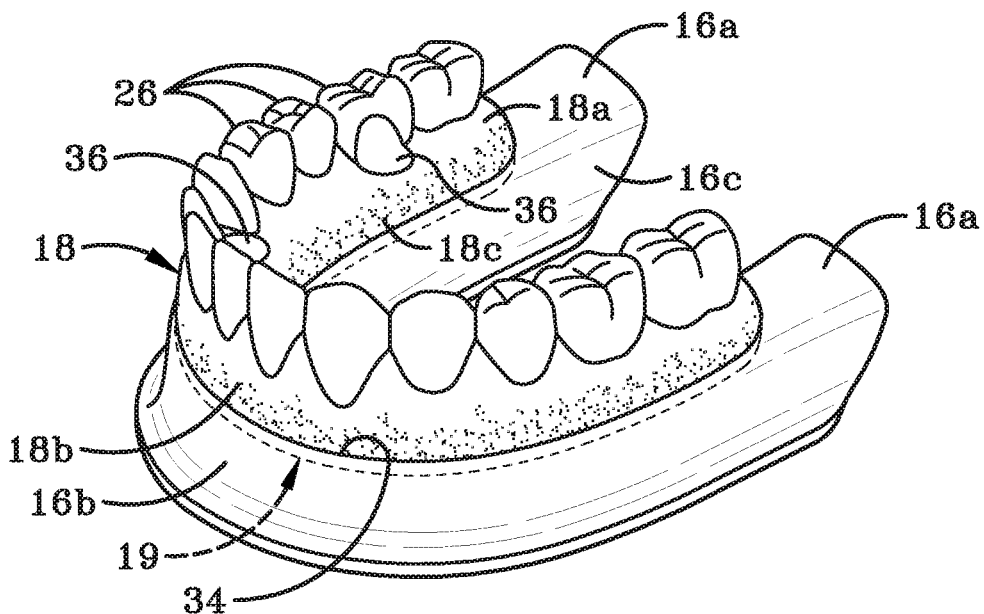
FIG. 4 is a perspective view of the final dental prosthesis shown engaged in the cradle of FIG. 1.

As is well known in the art, prosthesis 18 is configured to be complementary to at least a portion of jawbone 12 and gum tissue 22 when installed in the patient's mouth. Prosthesis 18 is shown in FIGS. 1, 3 and 4 as including a first wall 18a, a first sidewall 18b, and a second sidewall 18c. Prosthesis 18 includes a first region comprising a plurality of teeth 26 and a simulated gum 27, and a second region which is a sub-structure 19, preferably made of a non-reactive metal. A shallow channel 28 is defined in the interior surface of sub-structure 19, i.e., in the surface spaced from the simulated gum 27. Preferably, sub-structure 19 is fabricated from titanium and is fixedly secured to first wall 18a and generally forms part thereof. At least a portion of sub-structure 19 extends outwardly beyond the rest of first wall 18a, as is shown in FIG. 1.

Prosthesis 18 is secured to the patient's jaw using an anchoring assembly. The term "anchoring assembly" used in this description denotes any and all fixtures and fasteners that are known in the art for use in installing and securing a fixed prosthesis 18 in place. As such, anchoring assemblies may include, but are not limited to, securement members 35, for example pins; anchoring members, for example, implants 38; and screws 42. Anchoring assemblies may also in some instances include angled abutments. Securement members 35 are used for temporarily pinning surgical template 14 and, in accordance with the present invention, pinning cradle 16 in the patient's mouth, as will be described further herein. Implants 38 are configured to anchor prosthesis 18 to jawbone 12. Screws 42 are used to secure prosthesis 18 to implants 38 via cylinders 40, as will be described hereafter. The angled abutments may be engaged with the upper ends of implants 38, particularly if those implants are engaged with jawbone 12 at an angle that makes it difficult to secure prosthesis 18 thereto. If angled abutments are utilized, then screws 42 will be used to secure prosthesis 18 to those angled abutments. In accordance with the present invention, the anchoring assemblies also includes cylinders 40, i.e., cylindrical or sleeve type abutments. Cylinders 40 engage implants 38 and extend the length thereof into the oral cavity and particularly extend to engage prosthesis 18.

Figure 2A:
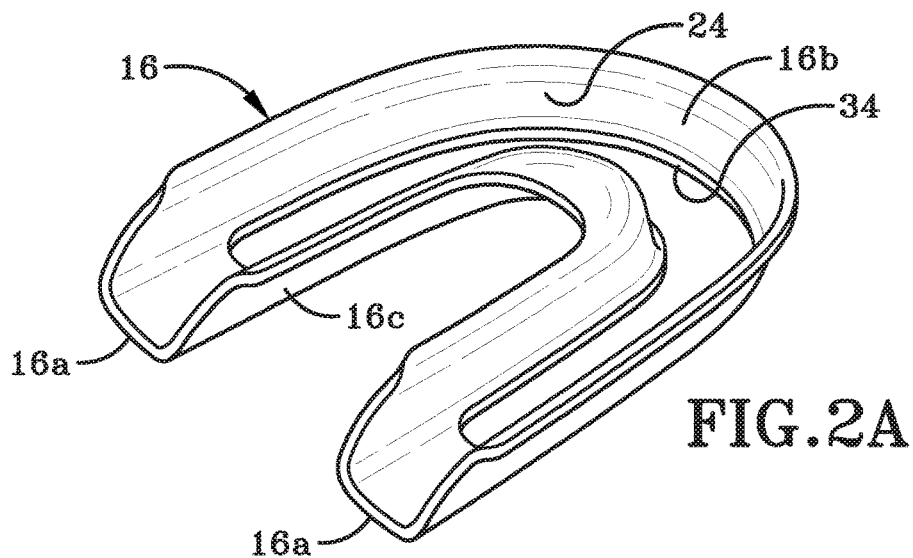
FIG. 2A is a perspective view of the cradle in accordance with the present invention shown in FIG. 1, which cradle is a first embodiment of the invention and is configured for placement on the patient's lower jaw, with the figure showing the interior surfaces of the cradle.

Referring to FIGS. 1 and 2A there is shown a first embodiment of a cradle 16 in accordance with the present invention. Cradle 16 is configured to be placed on a patient's lower jaw. Cradle 16 has been invented by the present inventor to be a type of "docking station" to correctly position and orient prosthesis 18 in the patient's mouth. More particularly, the use of cradle 16 diminishes the impact of positioning implants 38 at less than optimum locations or orientations within jawbone 12 relative to the locations and orientations selected by the computer program, as will be later described herein. In accordance with the present invention, the computer program and machinery which is utilized to fabricate surgical template 14 and prosthesis 18 is also programmed to design and fabricate cradle 16 using the data gathered during the CT scan of the patient's oral cavity. The computer program causes cradle 16 to be fabricated preferably out of the same material as surgical template 14, i.e., out of a composite resin or an acrylic material.

accordance with the present invention, cradle 16 includes a first wall 16a, a first sidewall 16b, and a second sidewall 16c. First wall 16a, first sidewall 16b and second sidewall 16c bound and define a channel 24 that is complementary to the contours of gum tissue 22 around jawbone 12. When cradle 16 is positioned over jawbone 12, top region 12a of jawbone 12 is disposed in channel 24 adjacent the interior surface of first wall 16a, front region 12b of jawbone 12 is disposed adjacent first sidewall 16b of cradle 16, and rear region 12c of jawbone 12 is disposed adjacent second sidewall 16c of cradle 16.

In accordance with yet another feature of the present invention, the computer program causes cradle 16 to be fabricated so that it includes an engagement means configured to be complementary to a portion of prosthesis 18. The engagement means enables prosthesis 18 to become engaged with cradle 16 when the two components are brought together. The engagement means on cradle 16 preferably is an elongate aperture 34 defined in first wall 16a. This aperture 34 is configured to be complementary to the peripheral edge of the titanium sub-structure 19 of final dental prosthesis 18. Cradle 16 and prosthesis 18 are configured to engage each other so that they act as a single unit. Sub-structure 19 may be snap-fittingly engaged in aperture 34 and have an interference fit therewith to substantially prevent prosthesis 18 from becoming accidentally disengaged from cradle 16. However, this interference fit is not absolutely necessary for the functioning of cradle 16 and sub-structure 19 may be somewhat loosely engaged in aperture 34.

Sub-structure 19 of the finished final prosthesis 18 defines at least one aperture, and preferably four apertures, 36 therein. Each aperture 36 is sized slightly larger than the maximum diameter of the implants. (In previously known final prosthetic devices, the titanium sub-structure included small screw holes through which screws were inserted to engage the implants. These small screw holes are sized exactly big enough to receive the small screws therethrough.) Each hole 36 in sub-structure 19 is configured to positionally align with one of the apertures 30 in surgical template 14. This arrangement ensures that each hole 36 will ultimately be able to generally align with one of the holes 32 drilled in jawbone 12. However, as indicated in the Background portion of the present application, during actual surgery the holes 32 are frequently not positioned sufficiently accurately enough that the holes 36 in prosthesis 18 will be able to align therewith. Consequently, in accordance with the present invention, the holes 36 formed in sub-structure 19 are made slightly bigger than the exterior diameter of the cylinders 40. Holes 36 in sub-structure 19 are therefore slightly bigger than the corresponding apertures 30 in surgical template 14. The slightly bigger holes 36 compensate for and allow slight or significant variations (in 3 dimensions) in the position of implants 38 which are inserted into holes 32 in jawbone 12. In other words, the slightly bigger holes 36 provide some tolerance in the system.

Figure 2B:
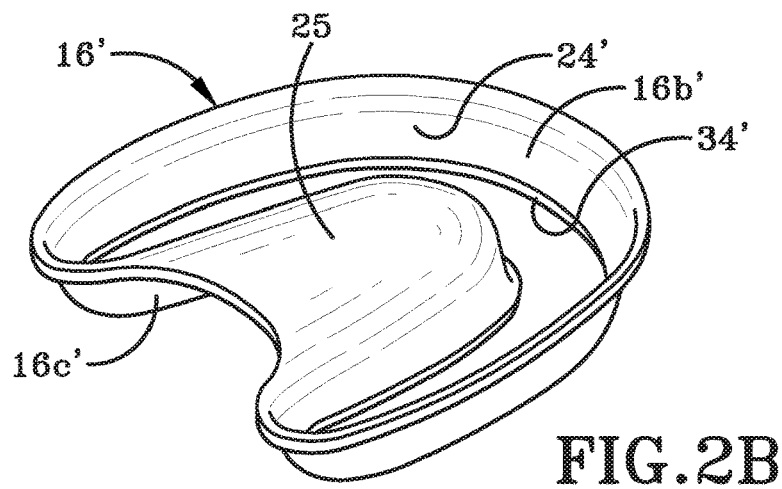
FIG. 2B is a perspective view of a second embodiment of the cradle in accordance with the present invention, with this second embodiment cradle configured for placement on the patient's upper jaw, and showing the interior surfaces of the cradle.

As illustrated in FIG. 2B, if the prosthesis 18 is to be placed on the patient's upper jaw, a slightly differently shaped cradle, indicated by reference character 16', is fabricated under direction of the computer program. Cradle 16' is substantially identical to cradle 16 and therefore includes a first wall 16a', a first sidewall 16b', and a second sidewall 16c'. However, cradle 16' also includes a palate region 25 which is complementary shaped to abut at least a portion of the patient's upper palate. Cradle 16' defines an aperture 34' therein that is configured to be complementary to the sub-structure on an associated prosthesis (not shown) for the patient's upper jaw. Cradle 16' is configured to snap-fittingly engage that sub-structure to secure cradle 16' and the upper jaw prosthesis together in the same fashion as cradle 16 engages prosthesis 18. Cradle 16' has the same exact dimensions as the dentures or wax dentures that were used during the CT scan. (It should be noted that this also true for cradle 16).

The present invention is used in the following manner. In a first guided method, the patient's oral cavity and denture is CT scanned as described previously herein in the Background portion hereof, and the data gathered during these scans is used to fabricate surgical template 14, the titanium sub-structure 19 for prosthesis 18, and, in accordance with the present invention, the new component i.e., the cradle 16. Surgical template 14 and cradle 16 take their dimensions from the denture used during the CT scan. The computer uses this information to generate a milled pattern replica out of a clear composite material that is identical to the denture relative to its tissue-fitting surface and border extensions. The parts are milled to different specifications depending on whether it's the surgical template 14 (which has typically four pre-drilled holes for implants 38) or a continuous aperture 34 in the case of cradle 16. The finished prosthesis 18 is exactly patterned off the scanned denture as well. Apertures 30 are drilled into surgical template 14 and are designed to position the implants, at the time of surgery, in exactly the same position in the mouth as designed on the computer. These pre-drilled apertures 30 are precisely extrapolated from the designed position of the implants. The optimum placement for the implants 38 is displayed on the computer but, as indicated previously, it is basically impossible for the dentist to attain this optimum placement of the implants 38 during the actual surgery.

The computer program will also generate a list of the required fixtures and fasteners that constitute the anchoring assemblies referenced earlier herein. These fixtures and fasteners are assembled into arrays for use during surgery. It should be noted that because of the introduction of cradle 16 into the system by the present inventor, the length of the cylinders 40 used in this type of surgery are custom milled and are considerably shorter than previously used temporary cylinders as described earlier herein for use with transitional prostheses. However, in the present invention which incorporates cradle 16, cylinders 40 are able to be made to the correct length so that they will typically not need to be cut down at all in order to be substantially flush with the mouth-facing wall of the prosthesis 18. This feature not only saves time for the dentist during installation of prosthesis 18 but also provides customized cylinders to meet the patient's exact specifications.

When all of the components of the system of the present invention are fabricated and the anchoring assembly arrays are ready, the manufacturer or supplier will ship a kit to the dentist which includes surgical template 14, prosthesis 18 including sub-structure 19, cradle 16 and the anchoring assembly arrays. All of these components will preferably be shipped to the dentist at the same time. As has been indicated previously herein, the prosthesis 18 used in the present invention is the final dental prosthesis for the patient, not a temporary or transitional component. Thus, the present invention preferably amalgamates all of the components for installation of the final dental prosthesis into a single shipment which, again, saves the manufacturer time and money. The present invention also saves the dentist time and money as he can perform the surgery all in one single visit instead of multiple visits as was the case with the previously known system. The present invention also saves the patient time, pain, mental trauma and inconvenience. This is because the surgery and installation is performed in a single visit and the patient is able to use the final dental prosthesis immediately and does not need to return to the dentist at a later time to have the final prosthesis placed. Because the patient goes home with the final prosthesis in place, they are immediately able to use their teeth as though they were their own.

Figure 5:
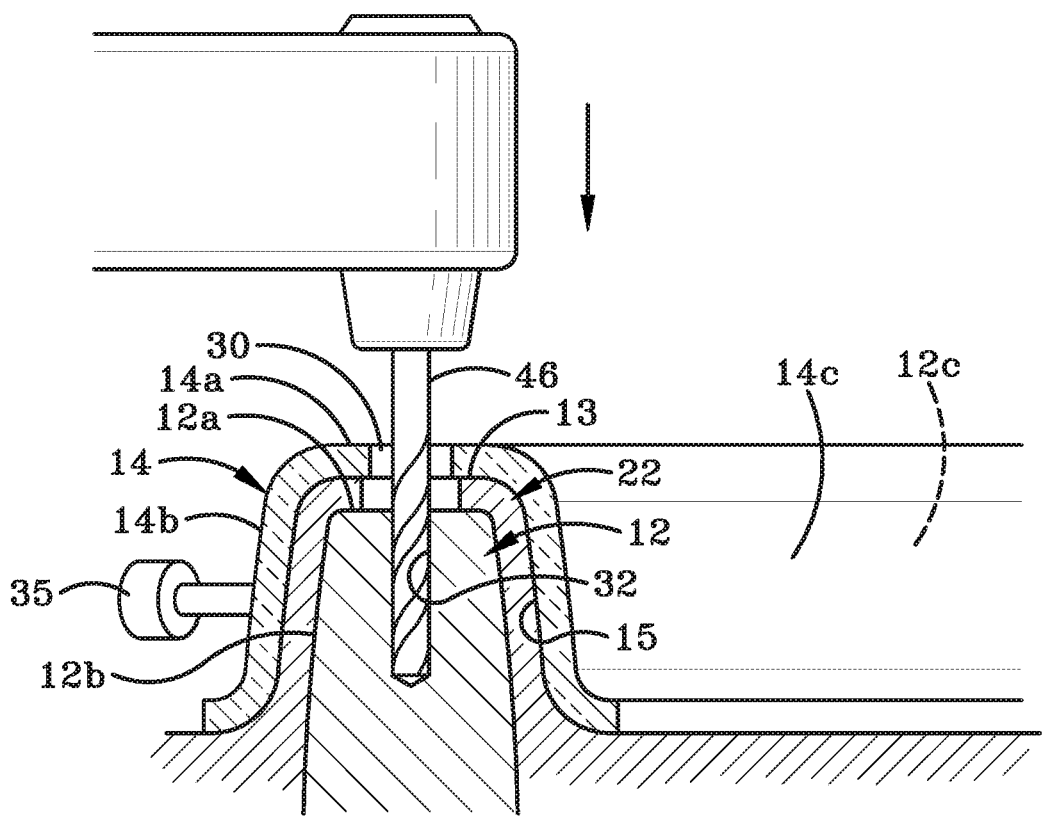
FIG. 5 is a cross-sectional view through the patient's lower jaw, showing the surgical template pinned to the jaw, and showing a pilot hole being drilled in the jawbone.

Referring to FIG. 5, once the surgery begins, the dentist will place surgical template 14 over the gum tissue 22 at the surgical site 13 on the patient's lower jaw. Surgical template 14 is designed and fabricated to include one or more holes (not shown) in first sidewall 14b and through which a securement member 35 is inserted to pin template 14 to jawbone 12. Securement members 35 are inserted generally at right angles to first sidewall 14b, through gum tissue 22 and into an area of the facial buccal bone. (A hole may be pre-drilled in the buccal bone to receive each securement member 35.)

Once surgical template 14 is properly pinned on jawbone 12, the dentist will remove a small plug of gum tissue 22 and then drill pilot holes 32 into jawbone 12 through apertures 30 of surgical template 14. The drilling is accomplished using a series of suitably sized drill bits as prescribed by the Nobel guide protocol.

Figure 6:
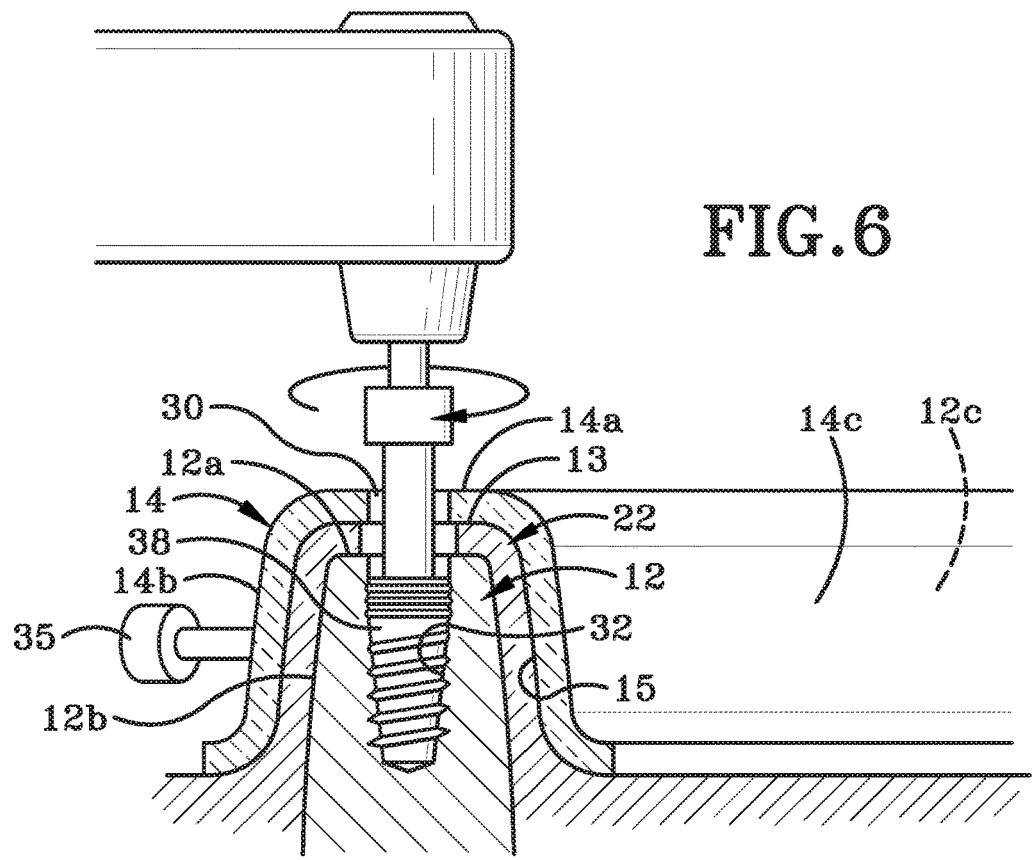
FIG. 6 is a cross-sectional view through the patient's lower jaw as shown in FIG. 5, and showing an implant being torqued into the jawbone.
Figure 7:
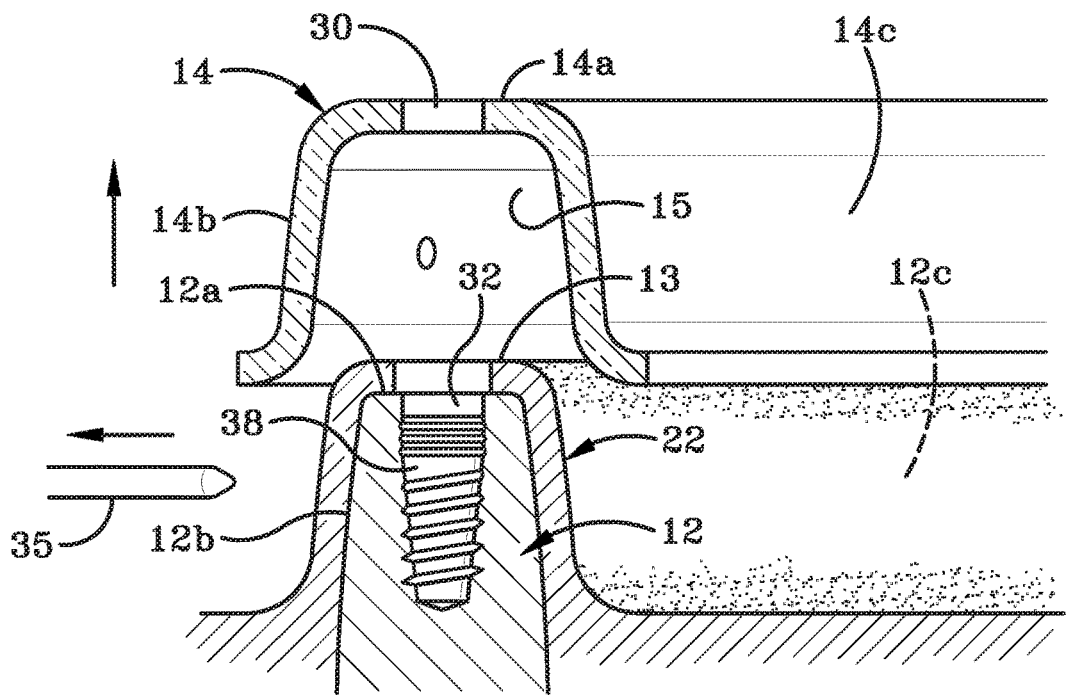
FIG. 7 is a cross-sectional view through the patient's lower jaw as shown in FIG. 6, showing the surgical template being removed from its placement on the lower jaw and showing the implant installed in the jawbone.

Referring to FIG. 6, implants 38 are then inserted through apertures 30 in surgical template 14, while it is still pinned in place, and into pilot holes 32. Implants are torqued or fixed into place in accordance with the manufacturer's specifications. If implants 38 are, for any reason, under or over-rotated into jawbone 12 during this procedure, it doesn't matter as the slightly oversized holes 36 in sub-structure 19 of final prosthesis 18 will compensate for this and will allow slight or significant variations in implant position (in three dimensions) to be managed. As shown in FIG. 7, once implants 38 are in place in jawbone 12, surgical template 14 is un-pinned (by removing securement members 35) and the template 14 is removed from the patient's mouth.

Figure 8:
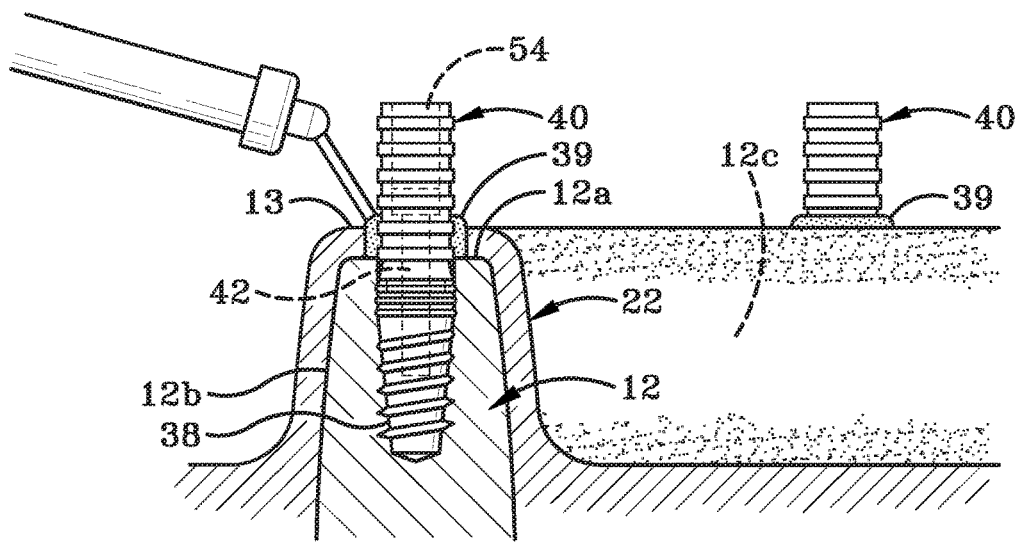
FIG. 8 is a cross-sectional view through the patient's lower jaw with a cylinder engaged with the implant and showing a block-out agent being applied around the base of the cylinder.

The custom-milled cylinders 40 are initially independent of final prosthesis 18 and are joined thereto at the time of placement after surgery. FIG. 8 shows a cylinder 40 engaged with the upper region of each implant 38. A screw 42 (shown in phantom) is used to secure cylinder 40 to the associated implant 38. Polyvinyl Siloxane (PVS—also known as vinyl polysiloxane (VPS)) or any other suitable block-out material, referenced by the number 39, is then applied around the exterior base of each cylinder 40. The PVS is applied adjacent the surgical site 13 to prevent any acrylic or cement (to be applied later in the process) from contacting the gum tissue 22 and damaging or irritating the same. Cylinders 40 are now extending outwardly from top face 12a of jawbone 12, as shown in FIG. 8.

Figure 9:
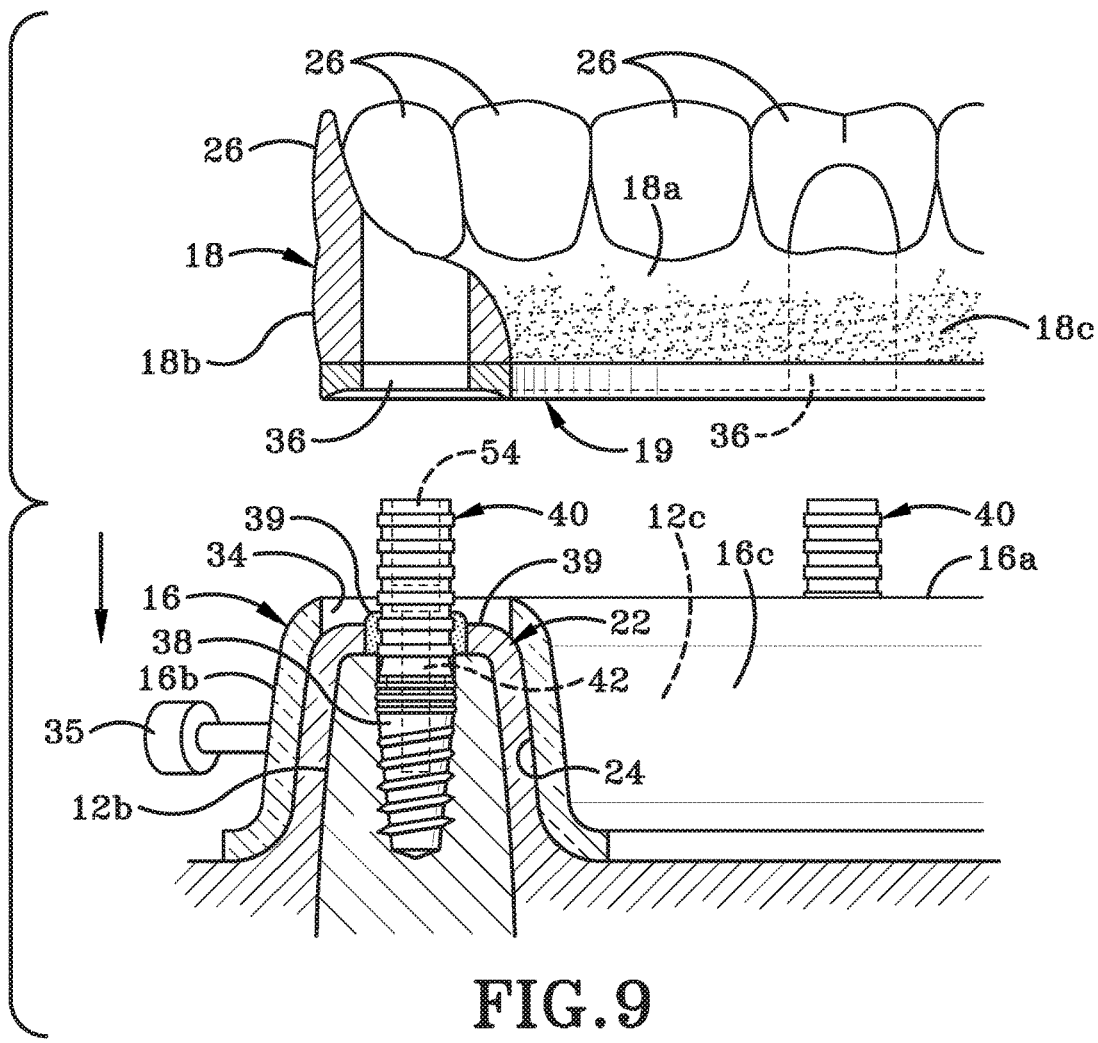
FIG. 9 is a cross-sectional view through the patient's lower jaw showing the cradle engaged with the jaw, the cylinder extending through an aperture in the cradle, and showing the final dental prosthesis being lowered into engagement with the cradle.

FIG. 9 shows cradle 16 being seated on the patient's lower jaw 12 such that the jawbone and surrounding gum tissue 22 is received in channel 24 of cradle 16. When cradle 16 is so seated, first wall 16a thereof is adjacent top face 12a of jawbone 12 i.e., adjacent surgical site 13; first sidewall 16*b* is adjacent first sidewall 12*b* of jawbone 12 and second sidewall 16*c* is adjacent second sidewall 12*c* of jawbone 12. Cylinders 40 extend outwardly through aperture 34 of cradle 16. Cradle 16, like surgical template 14, has one or more holes (not shown) fabricated in first sidewall 16*b* to receive a securement member 35 therethrough. Securement members 35 are engaged with cradle 16, with each pin 35 being inserted into one of the same holes (not shown) in the buccal bone as was used during pinning of surgical template 14. This arrangement temporarily secures cradle 16 in place in the patient's lower jaw so that it does not substantially shift thereon during engagement of prosthesis 18 with the engagement means, i.e., with aperture 34.

Figure 10:
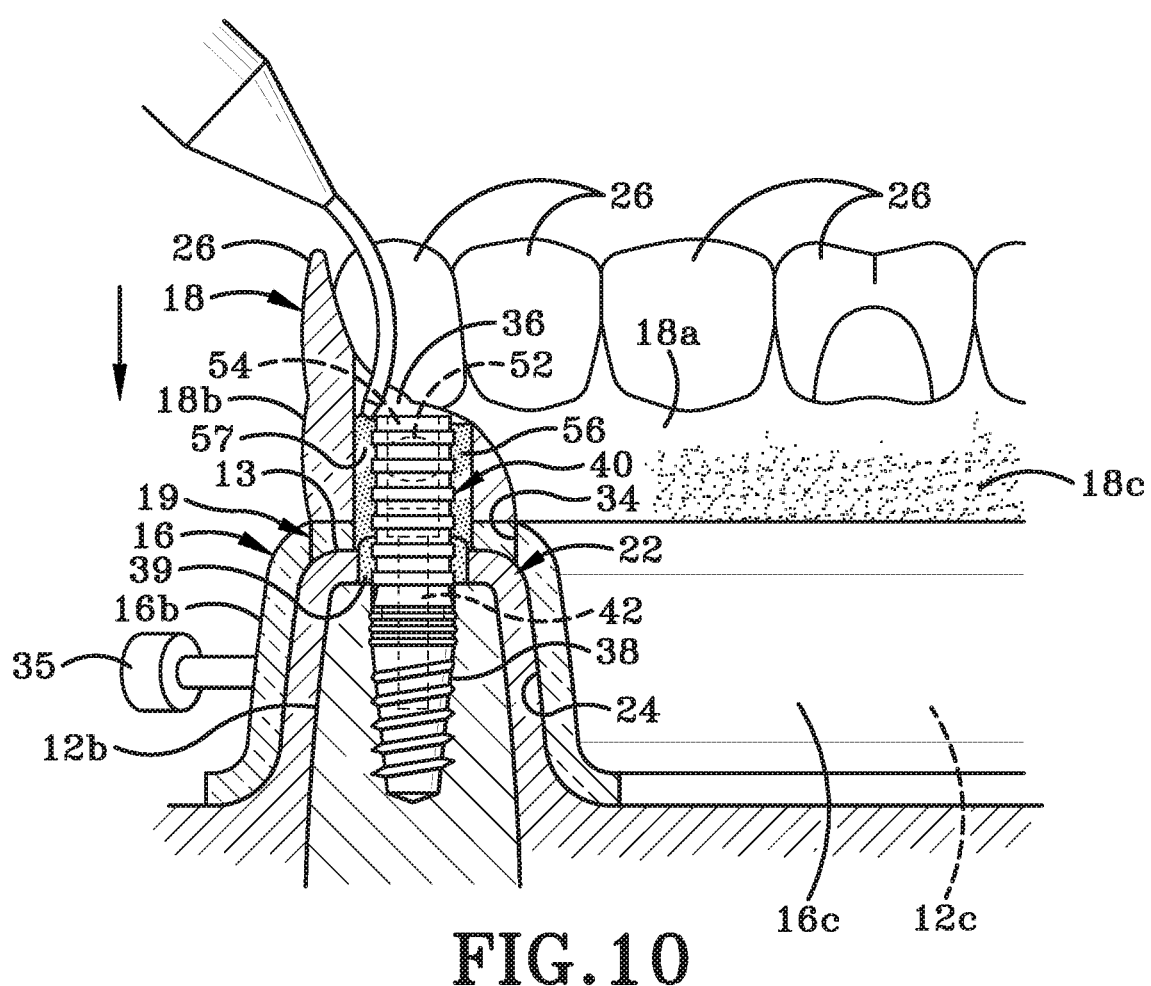
FIG. 10 is a cross-sectional view through the patient's lower jaw showing the final dental prosthesis engaged with the cradle, having the cylinder extending through a hole in the final dental prosthesis and showing a bonding agent being applied to bond the prosthesis and cylinder together.

Prosthesis 18 is then lowered onto cradle 16 and into engagement therewith as shown in FIGS. 9 and 10. Specifically, sub-structure 19 of prosthesis is received into aperture 34 in cradle 16. Preferably, sub-structure 19 is snap-fitted into aperture 34. As this occurs, care is taken to ensure that each one of the cylinders 40 passes through its appropriate and prescribed hole 36 in sub-structure 19 without interference. When cradle 16 and prosthesis 18 are snapped together, they form the total pattern of the scanned denture. FIG. 10 shows the cradle 16 and prosthesis 18 engaged with each other in such a way that first wall 16*a* of cradle 16 is disposed adjacent an interior surface of sub-structure 19. More specifically, cradle 16 is received within a channel formed by an interior surface of sub-structure 19. FIG. 10 also shows prosthesis 18 positioned and oriented on the jaw by cradle 16, with cylinders 40 extending through holes 36 in sub-structure 19 of prosthesis 18. It will be understood that cradle 16 and prosthesis 18 may, alternatively, be snap-fittingly engaged with each other prior to cradle 16 being inserted into the patient's oral cavity and before securement members 35 are utilized to pin cradle 16 in place.

The interference fit between sub-structure 19 and cradle 16 ensures that prosthesis 18 is correctly positioned and oriented in the patient's mouth. Because of the slightly larger size of holes 36 in sub-structure 19 and because implants 38 are positioned in the jaw through apertures 30 in template 14, the improved tolerance of holes 36 ensures that one or more cylinders 40 do not accidentally engage a region of sub-structure 19 instead of passing through the holes 36 therein. The slightly larger holes 36 further ensure that cylinders 40 do not protrude into the mouth beyond prosthesis 18. Thus, prosthesis 18 is oriented in exactly the same position, in three dimensions, as set up on the computer and in the lab ensuring exact aesthetics, bite, occlusion, vertical dimensions of occlusion (VDO) as set up in the lab and as per the CT scan.

If there is no interference fit between cradle 16 and prosthesis 18, the prosthesis 18 will simply be loosely seated in aperture 34. During bonding of cylinders 40 to prosthesis 18 the dentist will simply hold the prosthesis 18 in contact with cradle 16, without departing from the present invention.

Figure 11:
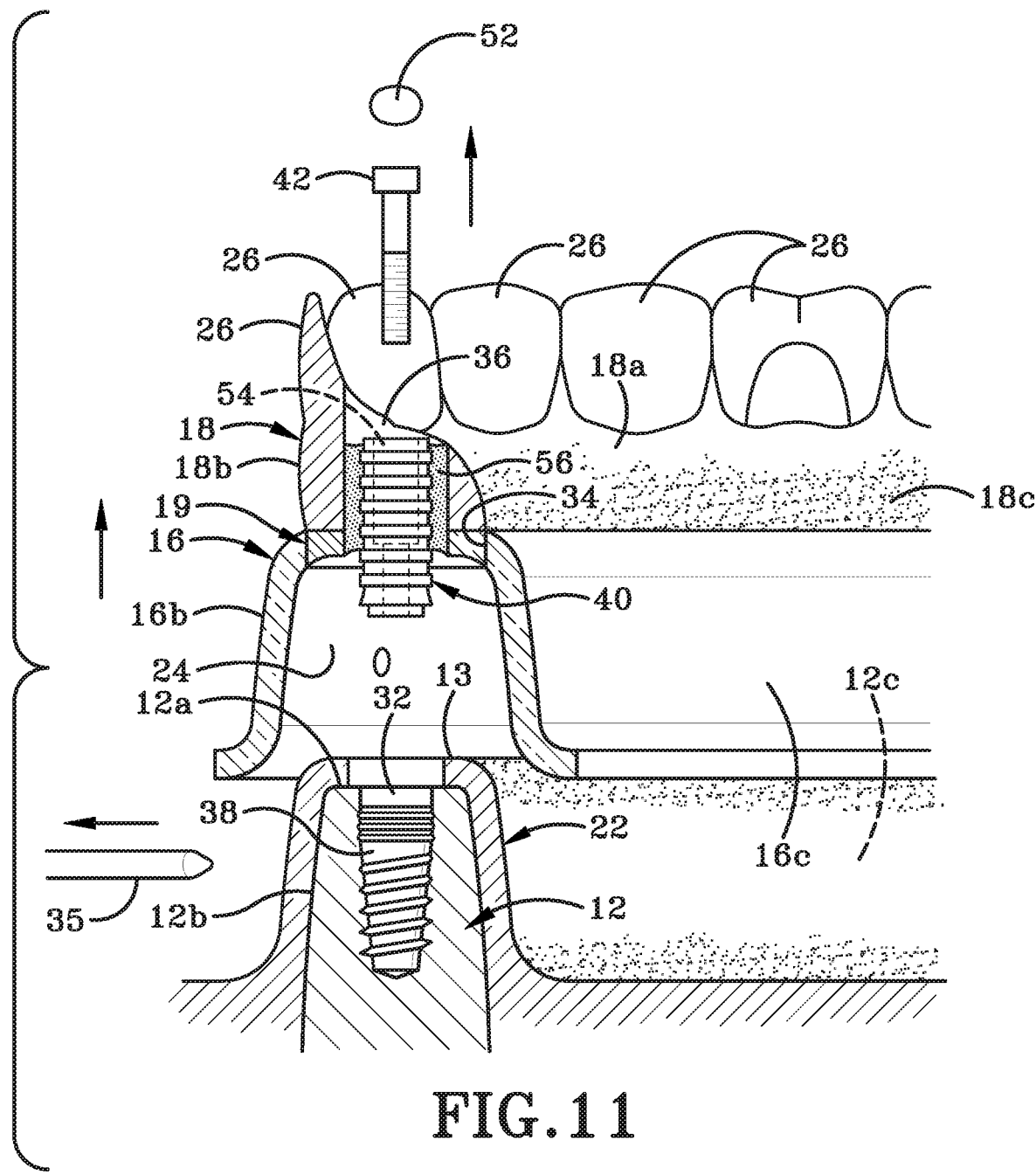
FIG. 11 is a cross-sectional view through the patient's lower jaw showing the prosthesis with the cylinder engaged therewith and the cradle being removed from the patient's lower jaw.

Referring to FIGS. 10 and 11, a cotton plug 52 is placed in the screw aperture 54 of each cylinder 40 to prevent that aperture 54 from being blocked during the next phase of the process. Cylinders 40 are luted to secure them to prosthesis 18, i.e., intra-oral acrylic cement or luting 56 is applied around the circumference of each cylinder 40 to fill up the hole 36 and to bond cylinder 40 and prosthesis 18 together. The luting 56 is given time to set. When the material has set, the cotton plug 52 is removed from each cylinder 40 and the associated screw 42 (shown in phantom) is unscrewed to break the engagement between the cylinders 40 and implants 38. Securement members 35 are withdrawn from cradle 16 and once this is completed, prosthesis 18 with cylinders 40 bonded thereto and with cradle 16 attached, is removed from the patient's jaw and his or her mouth.

Figure 12:
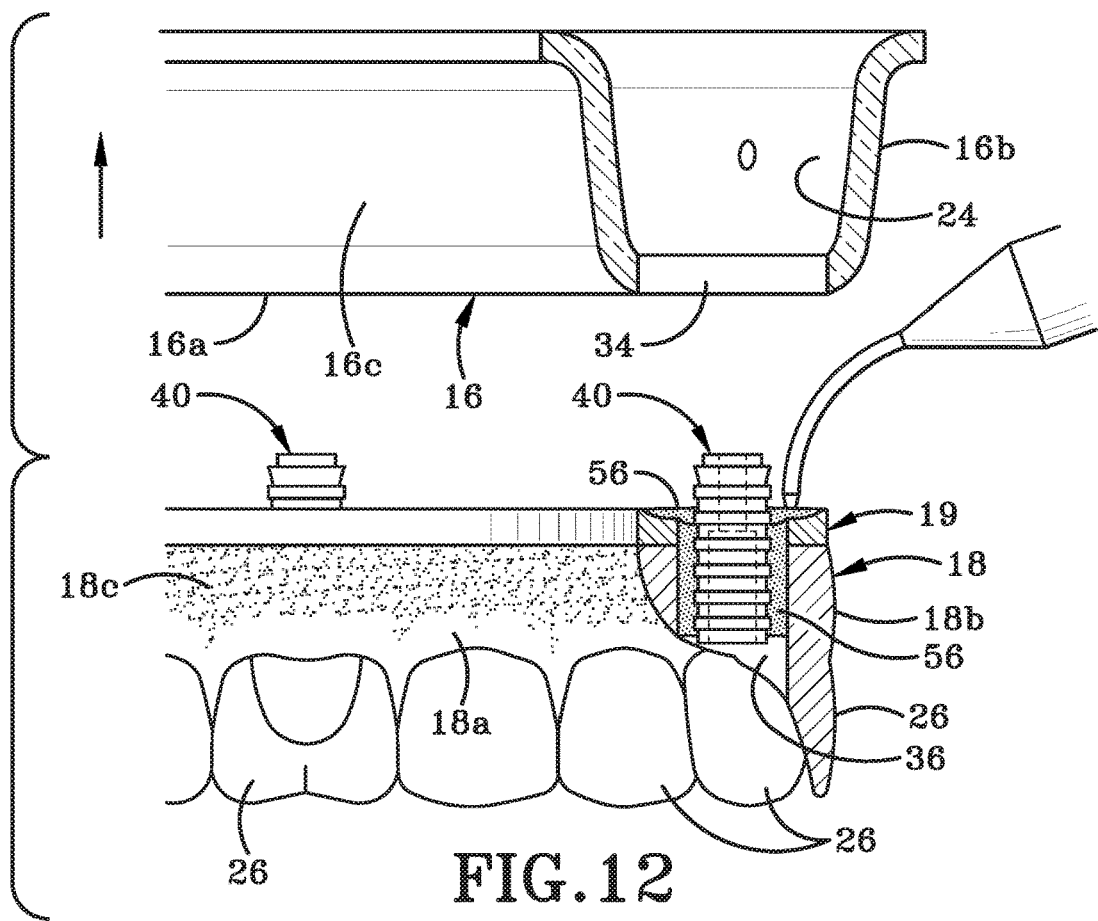
FIG. 12 is a partial cross-sectional view of the final dental prosthesis showing the cradle detached therefrom and showing a bonding agent being applied to a channel in the final dental prosthesis and around the bonded cylinder.

Cradle 16 is then detached from sub-structure 19 of prosthesis 18 (FIG. 12) and the prosthesis 18 with cylinders 40 still bonded thereto is cleaned to remove any excess acrylic or cement, as well as any blood therefrom. The channel area on the interior surface of sub-structure 19 surrounding cylinders 40 is then filled with acrylic cement 56. Acrylic cement 56 is also utilized to fill any hollows or gaps on the opposite side of prosthesis 18, particularly those surrounding cylinders 40. The cylinders 40 are now fixedly bonded to prosthesis 18 and are trimmed, if necessary. The prosthesis 18 is now completely ready for final placement, and it is polished and sterilized.

Figure 13:
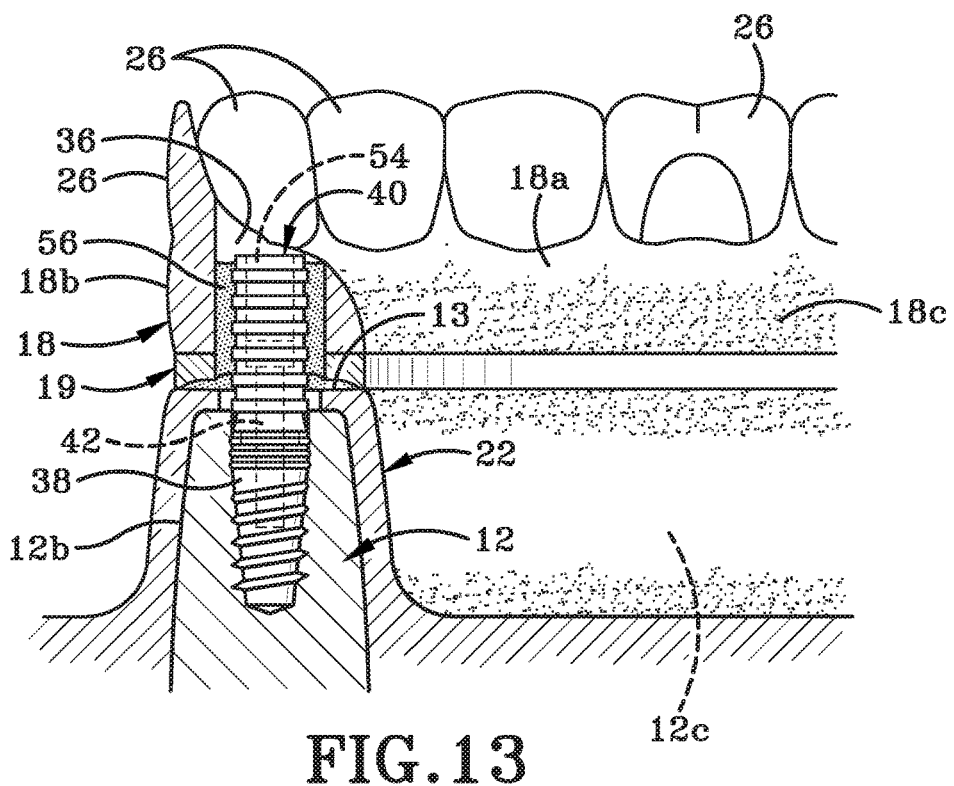
FIG. 13 is a cross-sectional view through the patient's lower jaw showing the final dental prosthesis placed on the jaw, with the cylinder engaged with the implant in the jaw and showing, in phantom, a screw securing the final dental prosthesis to the implant.

FIG. 13 shows prosthesis 18 being positioned for a final time in the patient's oral cavity so that it is seated adjacent the surgical site 13 on the patient's jaw, and so that the cylinders 40 engage the top regions of implants 38. A screw 42 (shown in phantom) is inserted through the aperture 54 of each cylinder 40 and is rotated to a sufficient degree to securely fix cylinder 40 and therefore prosthesis 18 to the associated implant 38.

It has been found that utilizing the devices, system, and methodology described above results in the dentist being able to take a patient from a substantially edentulous state to having the final prosthesis 18 secured in the correct orientation and position on the patient's jaw in around 3 hours. In the previously known system it typically took around 5-7 hours for a transitional prosthesis to be placed in a patient's oral cavity and the entire prior art procedure had to be redone in 6-8 months in order to secure the final prosthesis in the patient's mouth. Thus, the present invention has taken a time-consuming, labor-intensive, and technique-sensitive procedure and has reduced it to a single procedure that takes a few hours with the patient leaving the surgery with a final fixed prosthesis in place.

It will be understood that while the above description has indicated that the present invention is suitable for use with the Nobel Biocare ALL-ON-4 system, the present invention is also suitable for use with a wide variety of other dental systems such as those manufactured and marketed by Biomet 3i of Warsaw, Indiana.

Figure 14:
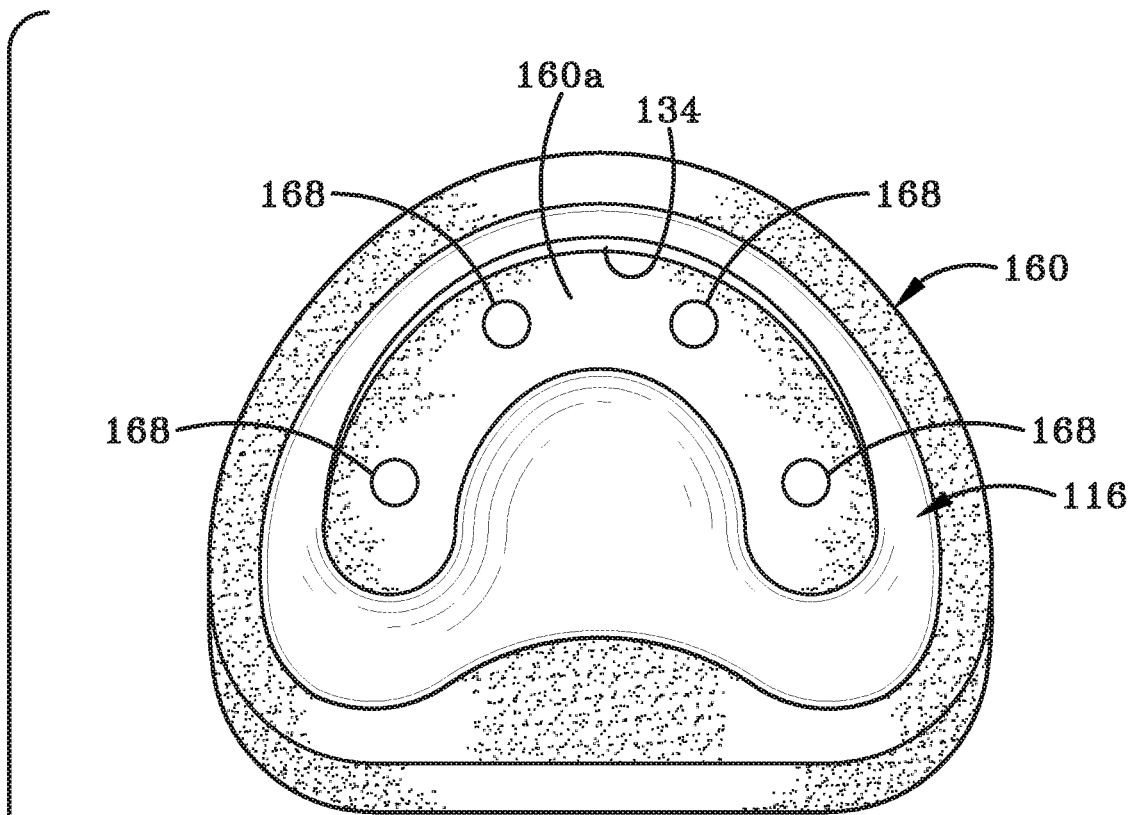
FIG. 14 is a top view of a cradle in accordance with the invention positioned on a mold and showing a separate titanium sub-structure that is separately cast or molded using the mold and is configured for subsequent engagement with the cradle.
Figure 14:
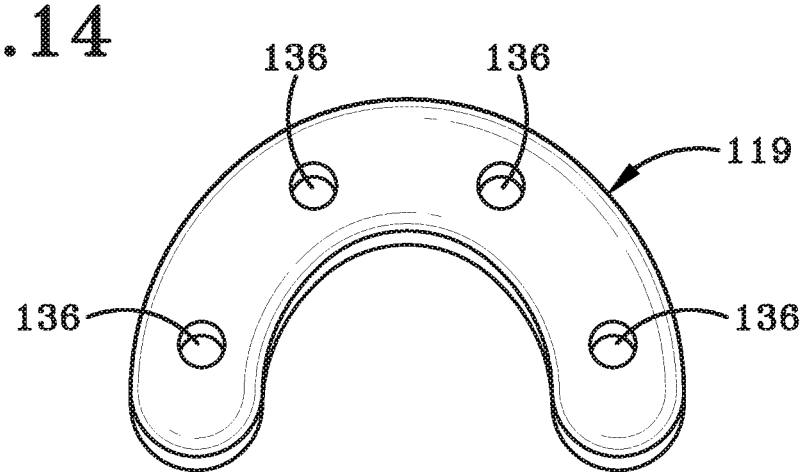

The above-described procedure is directed to the guided installation of prosthesis 18 incorporating the cradle 16 in accordance with the present invention. As previously indicated, it is also possible to install prosthesis 18 in a freestyle or unguided manner. The previously known freestyle or unguided installation has been described in the Background portion of this specification. In addition to the steps described in the Background and in accordance with the present invention, the dentist or dental technician will craft the cradle 16 in additional to crafting the prosthesis 18 and surgical template 14. Cradle 16 will be hand-made in the lab from an acrylic material by casting or molding the same to create the desired shape. FIG. 14 shows a plaster model 160 produced after the taking of an impression of the patient's oral cavity. An acrylic cradle 116 is crafted by the dentist or dental technician and is shown in this figure engaged on model 160. Cradle 116 defines a single aperture 134 therein and through which a region 160*a* of model 160 projects. Model 160 is also separately utilized to shape a titanium or cast sub-structure 119 which will be fixed to the dental prosthesis. The sub-structure 119 is substantially identical in shape to region 160*a* so that when sub-structure 119 is incorporated into the prosthesis, it will be able to snap-fittingly or interferencially engage cradle 116. Region 160a is shown with markings 168 thereon which signify the locations at which the dentist or dental technician will form apertures 136 in sub-structure 119. The apertures 136 perform the same function as apertures 36 in sub-structure 19. Cradle 116 performs the same function as cradle 16 and does so in the same manner.

When the surgical template (not shown but substantially identical to surgical template 14), cradle 116 and the final dental prosthesis incorporating sub-structure 119 (not shown but substantially identical to prosthesis 18) have been made by the dentist or dental technician, the rest of the method of utilizing these various components and placing the final dental prosthesis is substantially identical to the method described with reference to the guided installation.

Prior to the development of the present invention, Nobel Biocare would initially send two items to the dentist for the initial surgery, namely, the surgical template and the implants. Then several months later after another round of impressions, bite registration and try-ins, Nobel would send the dentist the final prosthesis. Even with the procedure as explained in the Background portion of this specification, on occasion, dentists would still find it necessary to make alterations to the final prosthesis before it could be seated properly in the patient's mouth.

With the system of the present invention, however, Nobel Biocare should be able to send one package to the dentist for the surgery. That single package will contain the surgical template, the implants, the cradle of the present invention, the final prosthesis, and all fixtures and fasteners necessary to accomplish complete installation of the final prosthesis. At the end of the surgery, the patient will leave the dentist's office in a matter of hours with their final, fixed dental prosthesis in place and ready for use.

While cradles 16, 16' and 116 have been illustrated and described as defining an aperture (34 or 34') therein and into which the sub-structure 19 for the dental prosthesis 18 is engaged, it will be understood that cradle 16 may be differently configured to have a different engagement means which will engage the dental prosthesis in some other manner without departing from the scope of the present invention. For example, the cradle may be formed to have two arms that are separated from each other by a gap, and the arms are configured to capture a portion of the dental prosthesis between them. Alternatively, the cradle may be provided with some type of clamping mechanism or fastening mechanism which could be temporarily engaged with the prosthesis to retain the cradle and prosthesis together in a substantially fixed orientation and position relative to each other.

Still further, the cradle 16 is described herein as being secured adjacent a surgical site 13 against movement by way of securement members 35. It is contemplated by the inventor that other types of securement means may be utilized to temporarily hold cradle adjacent the surgical site 13 without departing from the scope of the present invention. For example, instead of using securement members 35, some type of clamping mechanism or strap mechanism may be utilized to temporarily retain the cradle adjacent the surgical site 13. Any such different securement means may be used to substantially prevent cradle 16 from moving during engagement of prosthesis 18 therewith or during partial attachment of the prosthesis (when engaged with the cradle) to anchoring members in the tissue or bone at the surgical site 13. As indicated previously herein, the inventor contemplates that a cradle and securement means in accordance with the present invention could be used for positioning and orienting a wide variety of prostheses at their respective surgical sites.

It will be understood that if for some reason the titanium sub-structure is fabricated as more than one piece and bonded as such into final prosthesis 18, then cradle 16 would be configured with a sufficient number of apertures that are complementary to that differently shaped sub-structure 19 to permit the prosthesis and cradle 16 to be engaged with each other.

There are certain applications where it would be advantageous where the engagement means on the cradle 16 in accordance with the present invention is not a single continuous aperture, such as aperture 34. In such cases it is deemed necessary or desirable to have final prosthesis 18 not come into contact with gum tissue 22. In such cases prosthesis 18 would need to sit above the gum 22, without touching it. In these cases the cradle, which is not shown in the drawings, would function in exactly the same manner as cradle 16, with the exception that in fabrication the cradle would be formed to have at least one and preferably four apertures corresponding to the position of the implants 38 in jaw 12. These apertures would be slightly oversized to allow for variations in implant position as described earlier. The cylinders 40 for engagement with implants 38 would be fabricated to protrude through the apertures in the cradle and into the final prosthesis 18 through its similarly oversized holes 36. In this embodiment of the invention, the cradle would define a groove configured to be complementary to a portion of final prosthesis 18, preferably to sub-structure 19. This portion of the prosthesis 18 would snap-fittingly engage in the groove in the cradle in such a manner that prosthesis 18 would not become disengaged therefrom during installation. The previously described PVS (VPS), or any other suitable other block-out material, would be applied to the junction where the cylinders 40 meet the cradle (similar to the technique of applying the PVS (VPS) at the base of the cylinder where it meets the surgical site 13). This would ensure that the acrylic cement employed to bond the prosthesis 18 to the cylinders 40 doesn't inadvertently flow into the oversized holes in the cradle, thereby bonding the prosthesis 18 and cylinders 40 to the cradle. In such an application the cradle would be installed first, the holes therein be blocked out with PVS (VPS) and then the final prosthesis 18 snapped into the cradle's groove. This method of 'floating' the prosthesis above the gum for hygienic purposes is regularly employed in the known art. When the cradle in accordance with the present invention is incorporated into the installation procedure, the cradle, with it's grooved versus aperture configuration, accommodates this "floating" technique.

It should be understood that should a dentist determine that it is necessary, for some reason, to utilize a transitional prosthesis prior to installing the final prosthesis, the cradle in accordance with the present invention can be used to install a transitional prosthesis as well as subsequently be used to install the final prosthesis. The use of the cradle in the installation of the transitional prosthesis using the above-described method removes all of the problems associated with prior placement protocols. Thus, when the term "final prosthesis" is used in this specification, it should also be understood to also include transitional prostheses under conditions where the cradle in accordance with the present invention is used to place the same.

It is contemplated by the inventor that in some instances it may not be necessary, possible, or desirable to utilize cradle 16 during the installation of the final prosthesis 18. As has been indicated previously herein, the presently known system has not been able to permit a dentist to complete the installation of a final prosthesis starting with the placement of the implants right through to securing prosthesis in place in a single visit to the dentist's office. The inventor has recognized that in some instances cradle 16 may be omitted from the process provided a change has been made to prosthesis 18 during fabrication. In accordance with the present invention, prosthesis 18 is fabricated to include titanium sub-structure 19. During the fabrication of sub-structure 19 one or more apertures 36 are formed therein. Each aperture 36 has an internal diameter of a first size. This first diameter is configured to be slightly larger than the maximum external diameter of the cylinder 40 which will ultimately be received therethrough. During installation of prosthesis 18, one or more implants 38 are installed in the patient's jaw and a cylinder 40 is engaged with each of those implants 38. Prosthesis 18 is then positioned on the patient's jaw so that cylinder 40 engaged with each implant 38 extends through one of the one or more apertures 36 in prosthesis 18. In accordance with a particular feature of the present invention, the difference in size between the exterior diameter of each cylinder 40 and its associated aperture 36 is such that a gap 57 is defined between them. This gap 57 gives final prosthesis 18 the tolerance it needs to accommodate implants 38 being installed in the jaw in a location other than the optimum location computed by the computer. Once prosthesis 18 is positioned on the jaw with the one or more cylinders 40 extending through the associated one or more apertures 36, it is possible to secure prosthesis 18 to the one or more implants 38. This is accomplished by securing cylinder 40 to the associated implant 38 and securing cylinder 40 to prosthesis 18. Cylinder 40 preferably is secured to its associated implant 38 by screwing a screw 42 through the bore of cylinder 40 and into implant 38. Cylinder 40 is secured to prosthesis 18 by closing gap 57 between the exterior wall of each cylinder 40 and that portion of prosthesis 18 which defines the associated aperture 36 through which cylinder 40 extends. This gap 57 may be closed in any number of ways. As disclosed in the attached figures, gap 57 is closed by applying a bonding agent, such as cement 56 into gap 57 and allowing the cement 56 to set to secure cylinder 40 and prosthesis 18 together. Other methods of closing gap 57 may be employed without departing from the scope of the present invention. For example, some type of mechanical bridging may be applies between the exterior wall of cylinder 40 and prosthesis 18. Alternatively, cylinder 40 may be of a type that is able to expand so that its exterior wall advances toward the portion of prosthesis 18 which defines aperture 36. In this latter instance, cylinder 40 will ultimately have an interference fit with the portion of prosthesis 18 defining aperture 36. It will also be understood that a combination of these bonding agents, bridging mechanisms or mechanical mechanisms may be utilized to secure cylinder 40 to prosthesis 18. The entire installation procedure from the placement of the implants 38 to the securement of the final prosthesis thereto, is able to be completed in a single visit to the dentist's office.

The present invention is also contemplated for use in surgeries other than dental surgeries for the installation of other types of prosthetic devices. In particular, the invention is contemplated to be useful for retaining other types of prosthetic devices in fixed orientations and positions so that the prosthetic devices are able to be more accurately positioned at the surgical site than is currently possible. The inventor contemplates that a docking station/cradle type device could be configured to interlockingly engage with prosthetic components used in hip replacement surgery, knee replacement surgery, or other orthopedic procedures, for example. The cradle would be fabricated to be complementary to the prosthetic it is to hold in the correct position and orientation. The cradle will hold the prosthetic component in the desired orientation and position during initial installation of anchoring or fastening members to secure the prosthetic component in place. The cradle would then be disengaged from the prosthetic component and the installation of the anchoring or fastening devices would be completed. The inventor further contemplates that the use of a cradle to position and orient a prosthetic device could also be used in veterinary applications where the patient would be an animal.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A method of engaging a plurality of different dental components to a patient's jawbone comprising:
   providing a first dental component and a second dental component;
   providing one or more anchor pins;
   placing the first dental component on a region of the patient's jaw;
   inserting each of the one or more anchor pins through a wall of the first dental component and into an associated one of one or more receiving holes formed in the patient's jawbone;
   temporarily holding the first dental component in a desired position on the region of the patient's jawbone using the one or more anchor pins;
   performing a first dental procedure on the patient's jawbone while the first dental component is retained in position on the patient's jawbone by the one or more anchor pins;
   removing the one or more anchor pins;
   removing the first dental component from the region of the patient's jaw;
   placing the second dental component on the region of the patient's jaw;
   utilizing the one or more anchor pins as reference points for locating the second dental component in a correct position on the patient's jaw; and
   inserting each of the one or more anchor pins through a wall of the second dental component and into the associated one of the one or more receiving holes previously formed in the patient's jaw.

2. The method as defined in claim 1, further comprising:
   holding the second dental component on the region of the patient's jawbone using the one or more anchor pins.

3. The method according to claim 2, further comprising:
   installing one or more implants in one or more implant holes drilled in the patient's jaw.

4. The method according to claim 2, wherein holding the second dental component on the region of the patient's jawbone using the one or more anchor pins is temporary.

5. The method according to claim 3, further comprising:
   engaging a cylinder with one of the one or more implants such a portion of the cylinder extends outwardly from the patient's jaw; and positioning a dental prosthesis over the patient's jaw such that the portion of the cylinder extends through an aperture defined in the dental prosthesis.

6. The method according to claim 5, further comprising bonding the cylinder to the dental prosthesis.

7. The method according to claim 6, further comprising:
placing a dental prosthesis positioner device between the dental prosthesis and the patient's jaw prior to bonding the cylinder to the dental prosthesis.

8. The method according to claim 7, further comprising:
correctly orienting the dental prosthesis on the patient's jaw with the dental prosthesis positioner device.

9. The method according to claim 7, further comprising:
removing the dental prosthesis positioner device from between the dental prosthesis and the patient's jaw after bonding the cylinder to the dental prosthesis.

10. The method according to claim 9, further comprising:
inserting a screw through the cylinder and into the one of the one or more implants; and
securing the dental prosthesis to the patient's jaw with the screw and the one of the one or more implants.

11. The method according to claim 1, wherein the one or more anchor pins are inserted through a wall of the first dental component and directly into the associated one of one or more receiving holes formed in the patient's jawbone.

12. The method according to claim 1, wherein each of the one or more anchor pins is inserted through a wall of the second dental component and directly into the associated one of the one or more receiving holes previously formed in the patient's jaw.

13. The method according to claim 12, further comprising performing a second dental procedure on the patient's jawbone while the second dental component is retained in position on the patient's jawbone by the one or more anchor pins.

14. The method according to claim 13, wherein performing the second dental procedure involves performing a different dental procedure than the first dental procedure.

15. The method according to claim 13, wherein drilling the one or more implant holes occurs during performance of one of the first dental procedure and the second dental procedure.

16. The method according to claim 14, further comprising removing the one or more anchor pins from the patient's jawbone and removing the second dental component from the patient's jawbone.

* * * * *